(12) United States Patent
Ein-Gal

(10) Patent No.: US 7,634,057 B2
(45) Date of Patent: Dec. 15, 2009

(54) RADIOTHERAPY SYSTEM WITH TURNTABLE

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 0 days.

(21) Appl. No.: 11/856,822

(22) Filed: Sep. 18, 2007

(65) Prior Publication Data

US 2009/0074140 A1 Mar. 19, 2009

(51) Int. Cl.
G21K 5/04 (2006.01)
G21K 5/08 (2006.01)
G21K 5/10 (2006.01)

(52) U.S. Cl. .............................. 378/69; 378/65; 378/68; 378/95; 378/150

(58) Field of Classification Search .................. 378/65, 378/68, 69, 195–197, 95, 150–153, 205; 600/427
See application file for complete search history.

(56) References Cited

U.S. PATENT DOCUMENTS

| | | | | |
|---|---|---|---|---|
| 2,552,592 A * | 5/1951 | Rush | ...................... | 297/195.11 |
| 3,783,251 A * | 1/1974 | Pavkovich | ...................... | 600/1 |
| 5,250,019 A * | 10/1993 | McGinley | ...................... | 600/1 |
| 5,471,516 A * | 11/1995 | Nunan | ...................... | 378/65 |
| 5,600,702 A * | 2/1997 | Pigg | ...................... | 378/180 |
| 6,733,175 B1 * | 5/2004 | Pigg | ...................... | 378/167 |
| 7,418,079 B2 * | 8/2008 | Schildkraut et al. | ........... | 378/65 |
| 2006/0285641 A1 * | 12/2006 | Scherch | ...................... | 378/65 |
| 2007/0208252 A1 * | 9/2007 | Makower | ...................... | 600/424 |
| 2007/0211854 A1 * | 9/2007 | Koshnitsky et al. | ........... | 378/65 |
| 2008/0317203 A1 * | 12/2008 | Ferrand et al. | ................. | 378/65 |

* cited by examiner

*Primary Examiner*—Edward J Glick
*Assistant Examiner*—Thomas R Artman
(74) *Attorney, Agent, or Firm*—Dekel Patent Ltd.; David Klein

(57) ABSTRACT

A radiotherapy system including a collimator operable to shape and steer a radiation beam in at least one dimension, a turntable for supporting a patient thereupon adapted to rotate the patient about a rotational axis, the patient having a target therein for irradiation by the radiation beam, a detector adapted for measuring a position of the target relative to the radiation beam, and a processor adapted to receive target positional data from the detector, the processor being in communication with the collimator for causing the collimator to steer the radiation beam in a direction to the target.

10 Claims, 2 Drawing Sheets

RADIOTHERAPY SYSTEM WITH TURNTABLE

FIELD OF THE INVENTION

The present invention relates to radiosurgery generally, and particularly to stereotactic radio surgery.

BACKGROUND OF THE INVENTION

Stereotactic radiosurgery provides a dose of radiation in a target volume in a patient. The target is irradiated at a multiplicity of orientations with finely collimated beams. The use of stereotactic radiosurgery to render tissue necrotic is well established and various systems are currently used for stereotactic radiosurgery. The prior art recognizes the need to confine radiation as much as possible to the target volume being treated. Generation of a desired dose pattern at the target volume is the objective of a treatment plan which takes into account limitations of the particular radiosurgical system used.

A typical implementation of LINAC (linear accelerator) scanning involves rotating the LINAC gantry about its horizontal axis which intersects the beam (orthogonally) and the vertical rotational axis of a couch at an isocenter. The patient is placed on the couch such that the target volume also intersects the isocenter. The gantry rotation causes a beam of radiation to trace an arc on a sphere surrounding the target. The heavy rotating gantry and couch are associated with added expense and reduced accuracy.

Another prior art implementation of LINAC beam scanning is by rotating the patient about a vertical axis which intersects the target and irradiating with a beam which is angled with respect to the axis. For example, U.S. Pat. No. 5,250,019 describes a radiotherapy system oriented toward irradiating patient's head. The system utilizes a stationary source, means for rotating the patient and means for positioning said patient's head.

There are disadvantages of the system of U.S. Pat. No. 5,250,019, such as for performing Intensity Modulated Radiotherapy (IMRT). For example, IMRT requires a precise mechanical coupling of the radiation beam to the patient's rotational axis, and target immobilization relative to the patient's rotational axis. The required precise mechanical coupling can be somewhat achieved, but with a relatively expensive subsystem. The immobilization requirement limits the application to the head only, whereby the target's position is fixed relative to a head frame via an invasive attachment, applicable only for a single use. As a result, fractionated treatments, which are required in performing IMRT, cannot be supported by such a system.

An additional shortcoming of the known radiotherapy systems is the need for a shielded vault in which the treatment takes place. Construction of such a vault is expensive and time consuming due to size requirements. Gantry and couch rotations result in radiation scattered into a large volume that has to be shielded. Large volume shielding prohibits usage of high quality shielding materials such as tungsten or lead due to the high costs.

SUMMARY OF THE INVENTION

The present invention seeks to provide improved apparatus and techniques for radiosurgery, as described more in detail hereinbelow.

In the present invention, in contrast with the prior art, a simplified radiotherapy system is provided with a turntable for turning a patient about a rotational axis, a detector and processor for controlling position and collimation of a radiation beam, and radiation shields for the radiation source and patient. It is also noted that U.S. Pat. No. 5,250,019 requires fixation of the target relative to the radiation beam and also requires some sort of means for moving the target with respect to the rotational axis. In contrast with the prior art, the present invention does not require fixation of the target relative to the radiation beam. Additionally, the present invention does not move the target relative to the rotational axis, rather the present invention uses beam steering to aim at the target and the target center does not necessarily intersect the rotational axis.

There is thus provided in accordance with an embodiment of the present invention a radiotherapy system including a collimator operable to shape and steer a radiation beam in at least one dimension, a turntable for supporting a patient thereupon adapted to rotate the patient about a rotational axis, the patient having a target therein for irradiation by the radiation beam, a detector adapted for measuring a position of the target relative to the radiation beam, and a processor adapted to receive target positional data from the detector, the processor being in communication with the collimator for causing the collimator to steer the radiation beam in a direction to the target.

The radiotherapy system may further include a radiation source for emitting the radiation beam. The system may further include a patient support device attached to the turntable for fixing at least a portion of the patient.

A radiation source shield may be provided that at least partially encapsulates the radiation source in a manner generally sufficient for meeting regulatory radiation protection requirements. A patient shield may be provided that at least partially encapsulates the patient in a manner generally sufficient for meeting regulatory radiation protection requirements.

The radiation source is preferably, although not necessarily, stationary, and may be housed, for example, in a gantry of a LINAC.

The turntable can rotate the patient in azimuth about a generally vertical rotational axis, for example. The turntable may be turned by an actuator and may be mounted on a movable cart.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
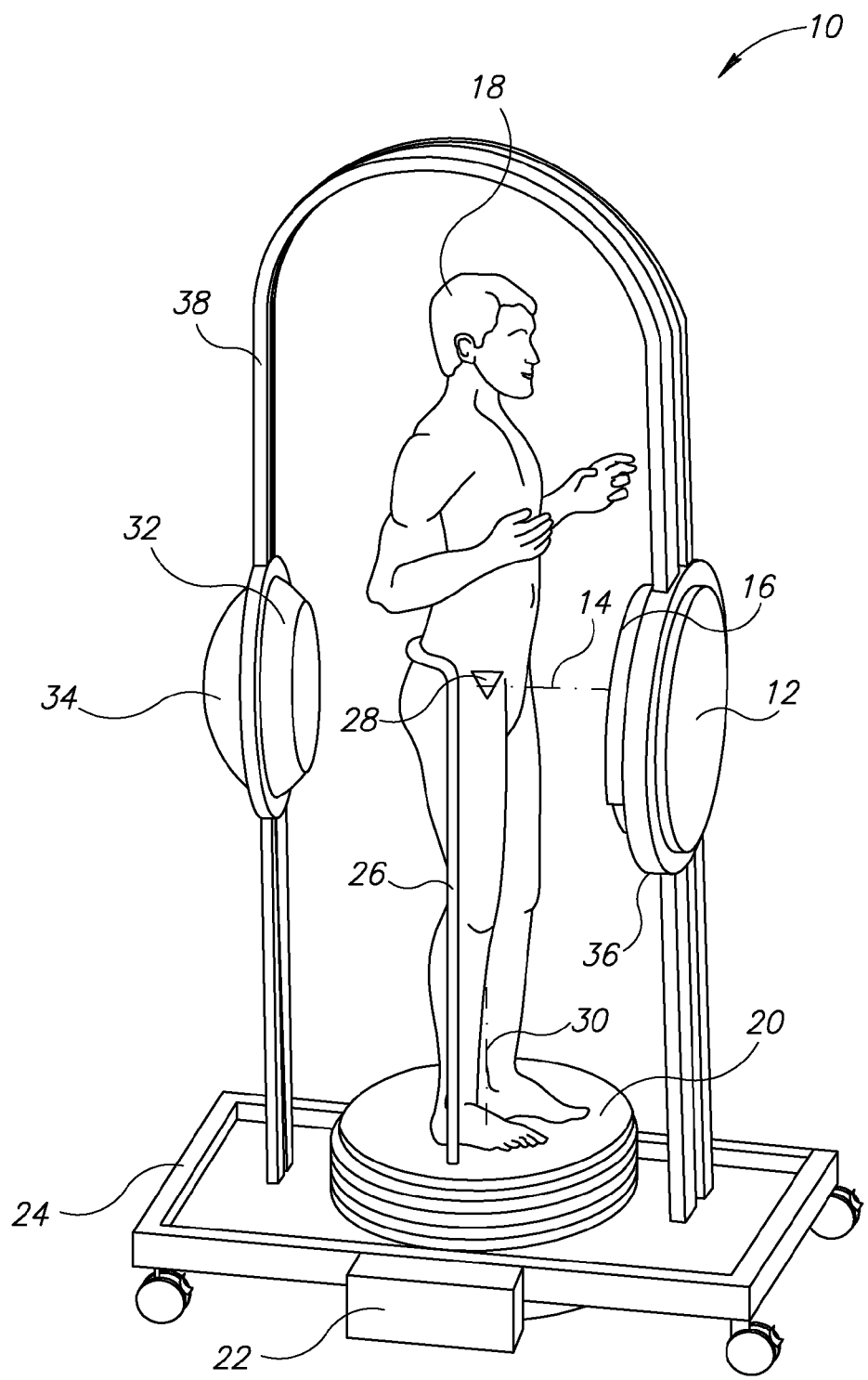
FIG. 1 is a simplified pictorial illustration of radiotherapy system constructed and operative in accordance with an embodiment of the present invention.

Reference is now made to FIG. 1, which illustrates a radiotherapy system 10, constructed and operative in accordance with an embodiment of the present invention.

Figure 2:
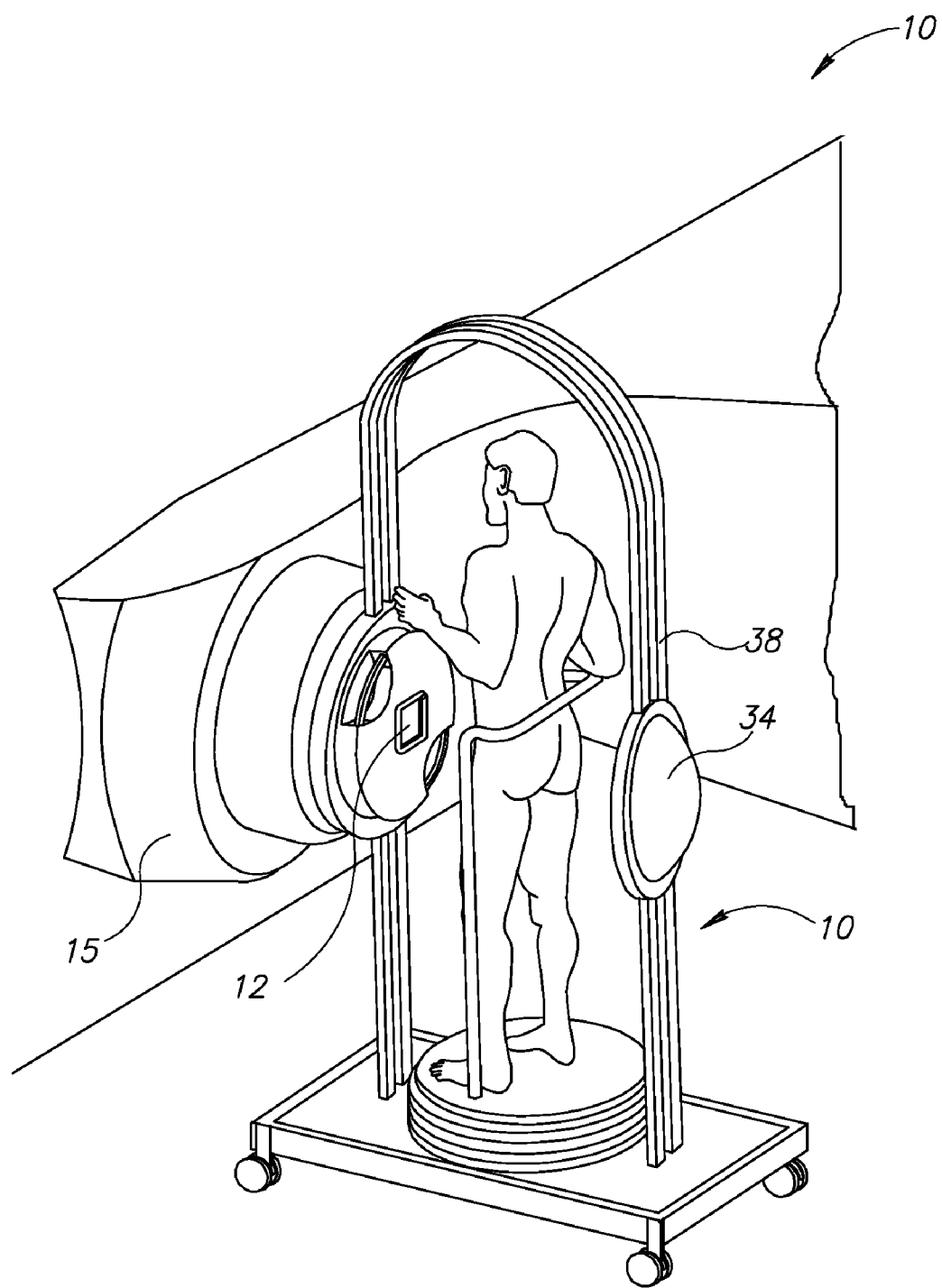
FIG. 2 is a simplified pictorial illustration of the radiotherapy system of FIG. 1, wherein the radiation source is housed in a gantry of a LINAC.

Radiotherapy system 10 may include a stationary radiation source 12 that emits a radiation beam 14. Although not necessary, radiation source 12 may be housed in a gantry 15 of a LINAC, as seen in FIG. 2. In the orientation of the figures, radiation beam 14 is generally horizontal, but it is understood the invention is not limited to a horizontal beam. A collimator 16 is operable to shape and steer radiation beam 14 in at least two dimensions (e.g., azimuth [around a vertical axis] and elevation [around an axis that is perpendicular to the page of the figure]).

A patient 18 may be supported on a turntable 20. Turntable 20 may be turned by a suitable actuator 22, such as a step motor or the like. Turntable 20 may be mounted on a movable cart 24. A patient support device 26 may be attached to turntable 20 and is designed to maintain at least a portion of the patient 18 containing a target 28 immovable during irradiation of the target 28. Turntable 20 is operable to rotate patient 18 in azimuth about a generally vertical rotational axis 30.

A detector 32 is provided for measuring the position of target 28 relative to the radiation beam 14. Detector 32 may be, without limitation, an accelerometer that senses and measures movement of patient 18 (and target 28 that moves together with each patient movement) with respect to radiation beam 14. As another example, target 28 may be monitored by fluoroscopy or other suitable medical imaging equipment. Generally, the medical imaging equipment forms an image of the area in which target 28 lies. This image is composed of pixels and it is well known in the art to detect and track the position of target 28 by sensing in which pixels the target appears. Since the beam position is known, in this manner one can readily measuring the position of target 28 relative to the radiation beam 14.

A processor 34 receives the target positional data from detector 32. The processor 34 is in communication with collimator 16 and can thus cause collimator 16 to steer radiation beam 14 in the target direction.

A radiation source shield 36 at least partially encapsulates radiation source 12 in a manner generally sufficient for meeting regulatory radiation protection requirements. A patient shield 38 at least partially encapsulates patient 18 in a manner generally sufficient for meeting regulatory radiation protection requirements. The shields may be constructed with lead or tungsten, for example.

Examples of "regulatory radiation protection requirements" are the US NRC (Nuclear Regulatory Commission) Regulations Title 10, Code of Federal Regulations, which define requirements binding on all persons and organizations who receive a license from NRC to use nuclear materials or operate nuclear facilities, Part 36—Licenses and radiation safety requirements for irradiators. Quoting therefrom:

"§ 36.25 Shielding.

(a) The radiation dose rate in areas that are normally occupied during operation of a panoramic irradiator may not exceed 0.02 millisievert (2 millirems) per hour at any location 30 centimeters or more from the wall of the room when the sources are exposed. The dose rate must be averaged over an area not to exceed 100 square centimeters having no linear dimension greater than 20 cm. Areas where the radiation dose rate exceeds 0.02 millisievert (2 millirems) per hour must be locked, roped off, or posted."

In operation, the patient 18 stands on turntable 20 and may be optionally held by patient support device 26. The target location is determined by any suitable method, such as computerized tomography or other medical imaging techniques. Processor 34 may process the information of the target location and communicate the information to collimator 16, which steers radiation beam 14 in the target direction. The positional information processed by processor 34 may also be used to position movable cart 24 and/or turntable 20 (with suitable movers or actuators) to provide coarse and fine adjustments of the position of patient 18 and target 28 with respect to the radiation beam 14. In this manner, for example, the positional information can be used to align the target 28 with the radiation beam 14 such that target 28 is located at an isocenter, that is, the intersection of radiation beam 14 with vertical rotational axis 30. Target 28 is then irradiated with a dosage of radiation at a first orientation. Turntable 20 can be turned at any desired azimuthal angle for subsequent irradiation at other angles, with the source of radiation 12 remaining stationary.

It is noted that the present invention does not require fixation of target 28 relative to radiation beam 14. Although target 28 can be adjusted to be at the isocenter, that is, at the intersection of radiation beam 14 with vertical rotational axis 30, nevertheless this is not essential to the invention. Rather the system of the present invention does not need to move target 28 relative to rotational axis 30, because collimator 16 uses beam steering to aim beam 14 at target 28 and the target center does not necessarily intersect rotational axis 30.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A radiotherapy system comprising:
   a collimator operable to shape and steer a radiation beam in at least two dimensions;
   a turntable for supporting a patient thereupon adapted to rotate the patient about a rotational axis, the patient having a target therein for irradiation by said radiation beam, wherein said turntable is mounted on a movable cart;
   a detector adapted for measuring a position of said target relative to said radiation beam, said detector comprising an accelerometer operative to sense and measure movement of the patient and said target that moves together with movement of the patient; and
   a processor adapted to receive target positional data from said detector, said processor being in communication with said collimator for causing said collimator to steer said radiation beam in a direction to said target, and wherein said processor is operative to process said target positional data to position said movable cart to adjust the position of the patient and the target with respect to the radiation beam.

2. The radiotherapy system according to claim 1, further comprising a radiation source for emitting the radiation beam.

3. The radiotherapy system according to claim 2, wherein said radiation source is stationary.

4. The radiotherapy system according to claim 2, wherein said radiation source is housed in a gantry of a LINAC.

5. The radiotherapy system according to claim 1, further comprising a patient support device attached to said turntable for fixing at least a portion of the patient.

6. The radiotherapy system according to claim 1, further comprising a radiation source shield that at least partially encapsulates said radiation source in a manner generally sufficient for meeting regulatory radiation protection requirements.

7. The radiotherapy system according to claim 1, further comprising a patient shield that at least partially encapsulates the patient in a manner generally sufficient for meeting regulatory radiation protection requirements.

8. The radiotherapy system according to claim 1, wherein said turntable is adapted to rotate the patient in azimuth about a generally vertical rotational axis.

9. The radiotherapy system according to claim 1, wherein said turntable is turned by an actuator.

10. The radiotherapy system according to claim 1, wherein said processor is operative to process said target positional data to position said turntable and said movable can to adjust the position of the patient and the target with respect to the radiation beam.

* * * * *